(12) United States Patent
Hettinger

(10) Patent No.: US 6,495,103 B2
(45) Date of Patent: Dec. 17, 2002

(54) MODULAR ANALYSIS CONTROL BLOCK

(75) Inventor: Christoph Hettinger, Ingelfingen (DE)

(73) Assignee: Burkert Werke GmbH + Co., Ingelfingen (DE)

( * ) Notice: Subject to any disclaimer, the term of this patent is extended or adjusted under 35 U.S.C. 154(b) by 0 days.

(21) Appl. No.: 09/171,919

(22) PCT Filed: Feb. 26, 1998

(86) PCT No.: PCT/EP98/01103

§ 371 (c)(1),
(2), (4) Date: Oct. 29, 1998

(87) PCT Pub. No.: WO98/39644

PCT Pub. Date: Sep. 11, 1998

(65) Prior Publication Data

US 2001/0048896 A1 Dec. 6, 2001

(30) Foreign Application Priority Data

Mar. 3, 1997 (DE) ..................................... 297 03 788 U

(51) Int. Cl.⁷ ............................. G01N 21/00; B01L 3/02
(52) U.S. Cl. ..................... 422/68.1; 137/269; 137/271; 422/81; 422/82; 422/100; 422/103
(58) Field of Search ................................ 137/269, 884, 137/271; 422/81, 82, 100, 103, 68.1

(56) References Cited

U.S. PATENT DOCUMENTS

| | | | | |
|---|---|---|---|---|
| 3,747,623 A | * | 7/1973 | Greenwood et al. ......... 137/269 |
| 3,863,666 A | * | 2/1975 | Bonne et al. ................ 137/269 |
| 3,881,513 A | * | 5/1975 | Chang ........................ 137/608 |
| 3,915,194 A | * | 10/1975 | Friedrich .................... 137/608 |
| 4,230,143 A | * | 10/1980 | Dettmann et al. .......... 137/270 |
| 4,726,929 A | * | 2/1988 | Gropper et al. .............. 422/68 |
| 4,819,877 A | * | 4/1989 | Ciccolallo et al. .......... 239/266 |
| 5,178,191 A | * | 1/1993 | Schaefer .................... 137/884 |
| 5,279,331 A | * | 1/1994 | Fernandez ................... 137/884 |
| 5,836,355 A | * | 11/1998 | Markulec et al. ........... 137/884 |
| 5,860,676 A | * | 1/1999 | Brzezicki et al. ............. 385/24 |
| 5,927,337 A | * | 7/1999 | LaMantia ................... 137/883 |
| 6,012,479 A | * | 1/2000 | Fukushima et al. ......... 137/271 |

FOREIGN PATENT DOCUMENTS

| | | |
|---|---|---|
| DE | 14 98 603 B | 11/1970 |
| DE | 38 18 148 A | 1/1989 |
| DE | 4008085 | * 9/1991 |
| DE | 94 06 393 U | 7/1994 |
| DE | 43 06 184 A | 9/1994 |
| DE | 195 15 524 A | 11/1996 |
| EP | 27256 | * 4/1981 |
| EP | 467479 | * 1/1992 |
| EP | 0 667 472 A | 8/1995 |
| EP | 0 735 302 A | 10/1996 |
| WO | WO 92 04568 A | 3/1992 |

OTHER PUBLICATIONS

E. H. Hansen et al. Anal. Chim. Acta 1978, 100, 151–165.*
E. Metzger et al. Anal. Chem. 1987, 59, 1600–1603.*
G. J. Moody et al. Analyst 1988, 113, 103–108, Jan. 1988.*
S Alegret et al. Anal Chim. Acta 1989, 222, 373–377.*

* cited by examiner

Primary Examiner—Arlen Soderquist
(74) Attorney, Agent, or Firm—Nixon Peabody LLP; Stuart J. Friedman

(57) ABSTRACT

A modular control block for applications in the field of analytical procedures has a plurality of individual elements (2, 5, 15, 19, 20), each having at least one channel for the inflow and for the outflow of fluids, which can be connected to each other by means of suitable connection points. In order to reduce the manufacturing costs of the control block, all individual elements (2, 5, 15, 19, 20) are embodied with the same outer contour and may be arranged in-line or staggered, with different function modes of the control block being achieved by either an in-line or a staggered arrangement of the individual elements (2, 5, 15, 19, 20), or by any desired combination of individual elements (2, 5, 15, 19, 20) arranged in-line and/or staggered.

8 Claims, 3 Drawing Sheets

MODULAR ANALYSIS CONTROL BLOCK

Figure 1:
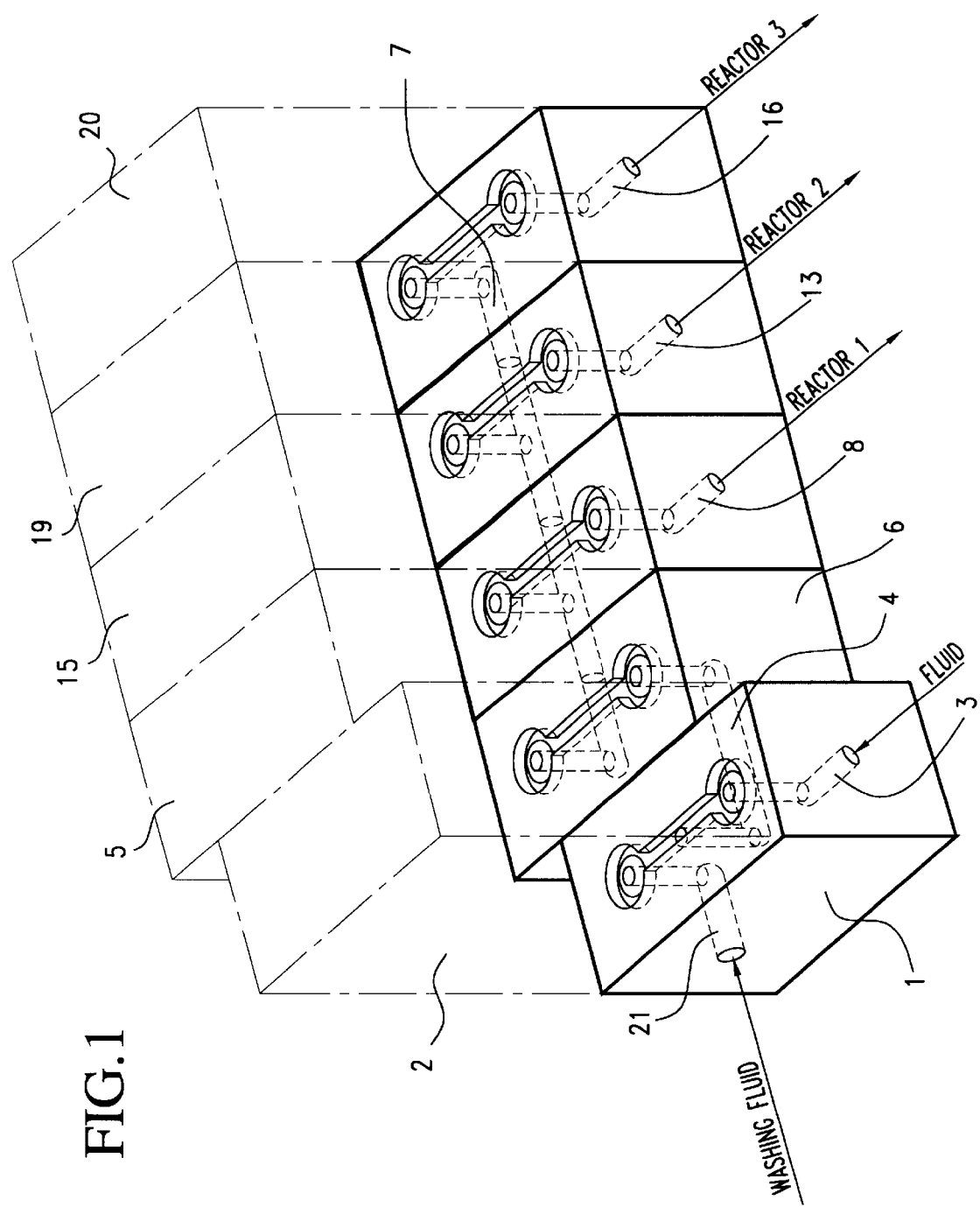

The invention relates to a modular control block for use in the field of analytical procedures. The invention is concerned in particular with the constructional design of a control block which may assume a plurality of different control functions, such as for example dosing, distribution, mixing or flushing, or a combination of these control functions, simply by a change in the line-up of the individual modules.

Such control blocks in modular design—in each case equipped with valves—are already successfully in use in other areas of control engineering, such as in pneumatic applications. Assembled as a combination of modular units, they provide very great flexibility and, the parts also being standardised, cost-effective production and warehousing is achieved.

So far there was no standardisation in the field of analytical procedures, as regards the interconnection of the valves and the components used, on account of the great variety of applications and of the complex ways of combination, as well as the high requirements exacted with respect to chemical resistance, reduced lost space, reduced gaps and internal volume.

Control blocks for applications in the field of analytical procedures are conventionally produced in such a way that a number of valves are so interconnected as to obtain the desired functions. To this purpose, mechanically machined control blocks, tailor-made to suit specific requirements, are produced, to which the valves are connected by means of flanges, to give an example. This method gives rise to rigid and cost-intensive control blocks which have to be designed and produced for each and every application requirement.

At a later time, furthermore, it is possible only at high expense in terms of cost and modification time to integrate sensors for the control of the medium, such as for flow measurements, into control blocks produced according to conventional methods. In most cases, sensors are then arranged before or after the control block; this gives rise to an increase of the internal volume and the lost volume.

It has been found to be a disadvantage in conventional control blocks for applications in the field of analytical procedures that for conventional unions between the individual elements of a valve block O-rings are used in preference, where lost space and gaps are not completely avoidable at the joining points.

A better solution is provided by the use of profiled O-rings or special form seals, but these are very expensive.

It is therefore the object of the invention to improve the control blocks for use in the field of analytical procedures in a way that both specific customer requirements may be complied with and that a standardisation of the blocks is realised, which will result in lower production costs because the units can be made in large production batches. Furthermore, and in accordance with the invention, the elements may be modified in such a way that sensors may be installed without lost space or gaps, if required. These sensors may serve, for example, the purpose of determining whether a flow exists in specific channels and of transferring the result to an electronic evaluation processor.

According to the invention, a modular control block for analytical procedures comprising a plurality of individual elements is provided for this purpose, the individual elements each containing at least one channel for the inflow and for the outflow of fluids, and being adapted to be connected to one another at appropriate points of connection, where all the individual elements have the same outer contour and may be arranged in-line or staggered, wherein different functional modes of the control block may be achieved by arranging the individual elements in line, staggered, or in a combined configuration of in-line or staggered individual elements.

The individual components of the modular control block according to the invention have the advantage that the outer shape and the position of the main channels is identical in all elements. In the case of the present invention, individual elements are used which may be combined in a number of different ways. The dimensional pattern of the connecting valves and sensor outputs is designed in such a way that both inflow and outflow ports may be controlled by means of electric bus lines which are normal in pneumatic systems. In a preferred embodiment, the control block is controlled via a multi-pole plug or a field bus.

The arrangement of the elements may be configured in different ways, depending on the application intended. If, for example, the elements are arranged in line without mutual shift, the functions realised mean that the fluids concerned flow within a common channel or are taken from a common channel. In the case of a staggered line-up, however, functions are created where the fluid flows through the elements one after the other. Even a combination of in-line arranged elements with mutually shifted elements is possible. The staggered arrangement is made possible by the fact that the connection bores in the individual elements are at the same height. In the case of the present invention, a plurality of multi-arrangements for the realisation of complex control functions is created by any desired combination of elements arranged in-line and/or staggered.

In a further development of the invention, the at least one channel is formed by a control bore, and the depth of the control bores differs for different individual elements. The position of the control bores, that is of the main channels, is identical for all elements, only the depth of the control bores differs, depending on the function of the element. By taking this measure it becomes possible to produce the individual elements as low-cost injection moulded parts only one die mould has to be produced for all the different embodiments. Modifications are created, for example, by the simple replacement of interchangeable shutters in the die mould.

It is furthermore of advantage that a sensor, for example for flow or temperature measurements, can be incorporated in each individual element produced in accordance with the invention. In order to insert the sensor free of lost space and gaps, each element is provided with one or more conical blind-end bores which become gradually narrower towards the main channel, and which are separated from it by a thin material layer. This thin layer will only be pierced when a sensor is installed.

In the case of the present invention, the sensor is inserted into a sleeve of an elastomer material and, together with it, is pushed into the ruptured conical bore. According to the invention, the conical bore serves the purpose of holding the unit, consisting of sleeve and sensor, in such a way that it is retained self-locking in the housing. The contact pressure of the sleeve is greatest in its frontal area, where the sensor protrudes from the sleeve into the channel, and therefore a jointing seal free of lost space and gaps is achieved for the sensor element. The fluid flows around the sensor. In a preferred embodiment, the area around the connecting electrical leads is filled with casting resin in the interest of electrical safety. In the case of a further embodiment, this area is made safe by means of a clamping element. This prevents the installed sensor from changing position.

In order to enable the modular valve block to be re-equipped with sensors in a simple way at a later date, for example with pressure sensors, the invention provides a special element for sensors which may be re-equipped without any need for modification of the modular control block. Such an element is simply connected to an existing individual element by means of a flange, instead of the connecting nipple. On the basis of the proposed arrangement, even in this case the design and assembly of both the housing and the sensor are such that no lost spaces or gaps are produced, which otherwise may lead to deposits as the area is washed by the fluids.

According to the present invention, transition points without lost space are achieved by the provision of recesses with a tapered bottom to accommodate the sealing elements. This ensures that the sealing element—preferably a rectangular seal—is subjected to a greater pressure towards the fluid carrying channel than on the side opposed to the fluid flow. In this way a jointing point is created which is hermetically sealed and free of lost space and gaps. There is then no need for expensive form seals; rectangular seals may be made at low cost of almost any sealing material.

Figure 2:
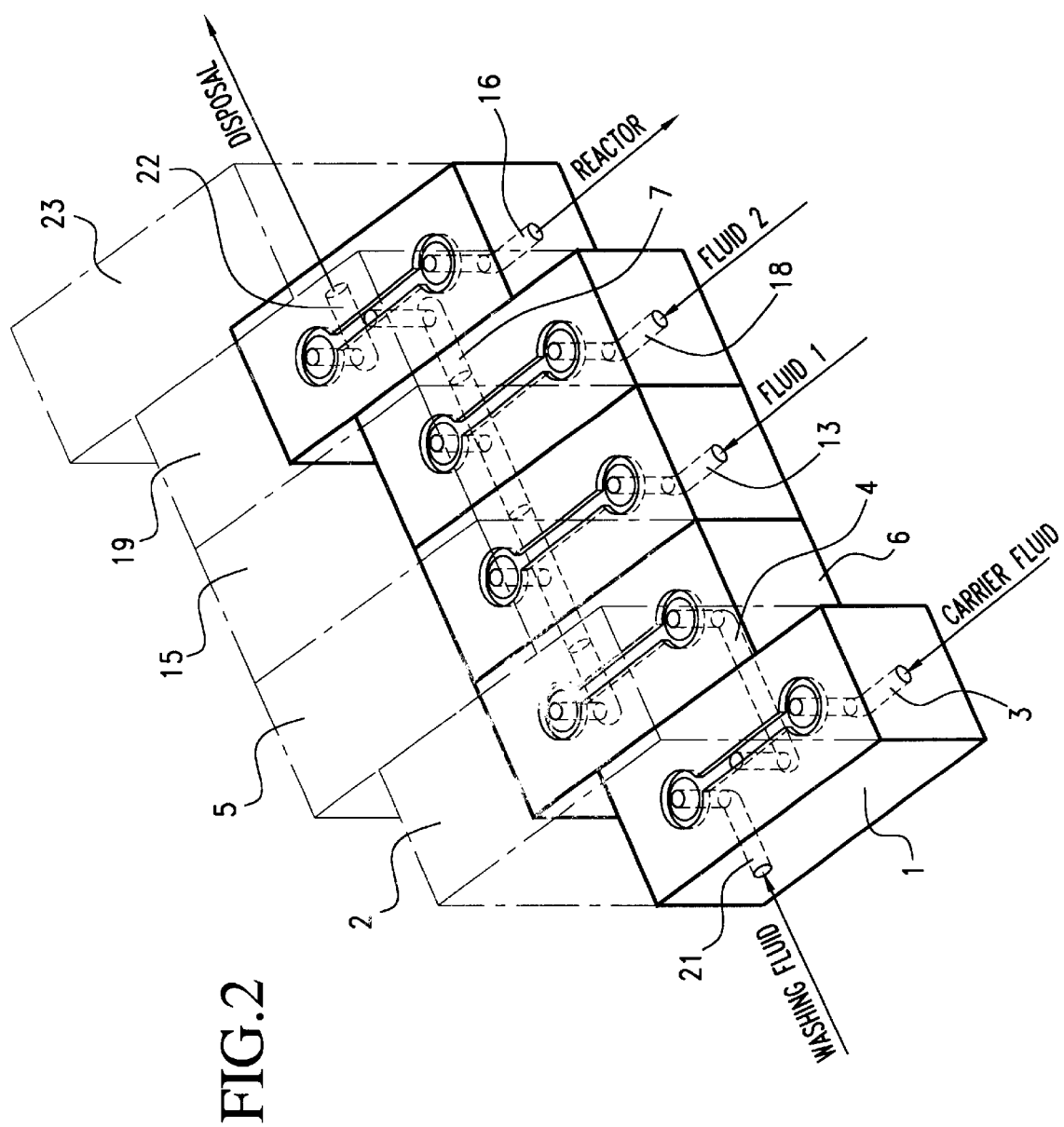
Figure 5:
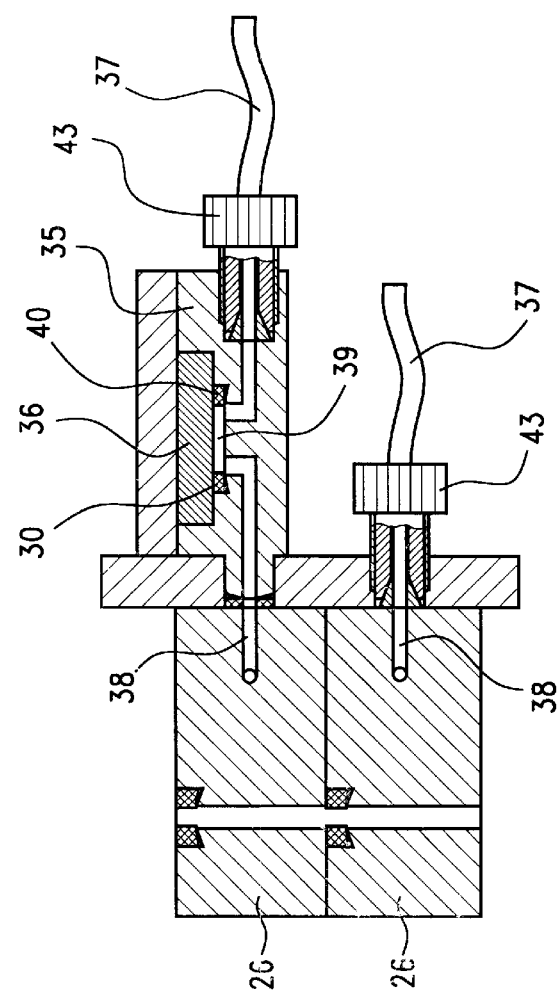
Figure 3:
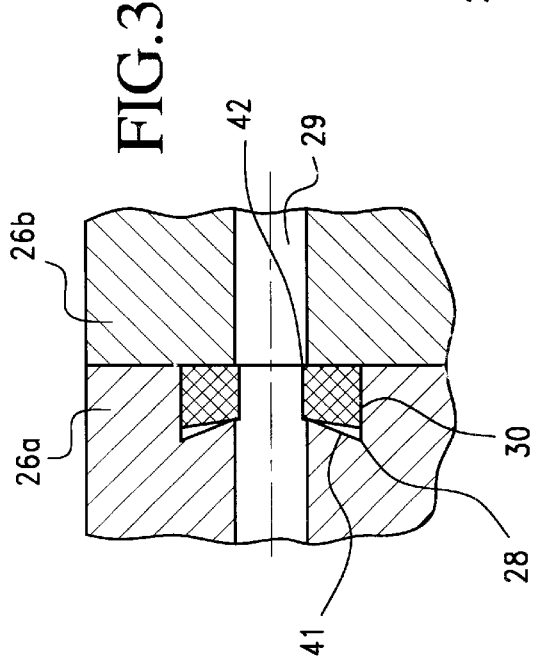
Figure 4:
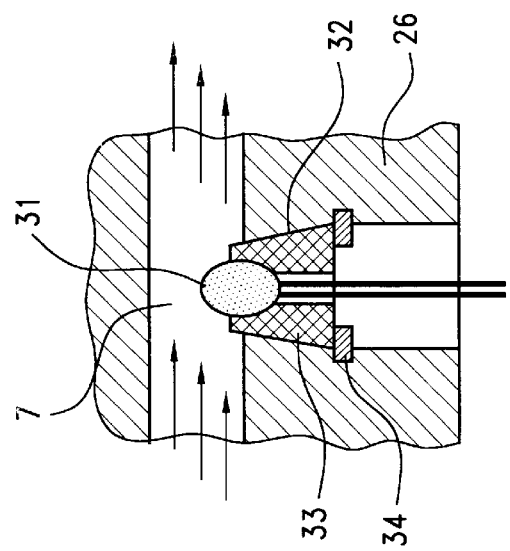

The invention is explained in more detail in the following description with reference to the embodiment examples illustrated in the drawings, where FIG. 1 shows a schematic representation of an arrangement of the individual elements for the application case "distribution" and "flushing", FIG. 2 shows a schematic representation of an arrangement of the individual elements for the application case "mixing" and "flushing", FIG. 3 illustrates a sectional representation through the joining point between the elements, FIG. 4 is a sectional representation through the bore in an element, with sensor installed, and FIG. 5 shows a sectional view through the re-equipment element with sensor.

FIG. 1 illustrates the application examples "distribution" and "flushing". In the application case "distribution", the 3/2 way valve (2) in the left-hand element (1) opens the inflow channel (3) for the fluid and directs this into the 2/2 way valve (5) of the second element (6) via the central bore (4). If the valve (5) in this element (6) is open, the fluid flows into the main channel (7) and can be supplied from there to the reactors, not shown in the drawing, via the feed channels (8, 13, 16) by opening of the 2/2 way valves (15, 19, 20).

For the flushing process, the supply of the fluid into the main channel (7) is interrupted by the 3/2 way valve (2). At the same time, the 3/2 way valve (2) and the 2/2 way valve (5) open up the flow of the washing fluid into the main channel (7) through the channel (21) via the central bore (4). From the main channel (7), the washing fluid flows via the valves (15, 19, 20) into the feed channels (8, 13, 16) and to the reactors.

FIG. 2 illustrates the combination of the elements which enables the function "mixing" of two fluids or the function "flushing" to be obtained.

For mixing, the 3/2 way valve (2) in the left-hand element (1) blocks the supply of washing fluid from channel (21) and allows a carrier fluid to flow from channel (3) via the central bore (4). When the 2/2 way valve (5) in the second element (6) opens, the carrier fluid flows into the main channel (7). At the same time, fluid 1 and fluid 2 flow from the channels (13, 18) through the 2/2 way valves (15, 19) into the main channel (7) and are fed to the reactor (16) via the 3/2 way valve (23), the switch position of which opens the channel to this reactor.

When in application mode "flushing", the 2/2 way valves (15) and (19) close, and the 3/2 way valve (23) cuts the flow of the fluid mixture from the main channel (7) to the reactor channel (16) and opens the way to the disposal channel (22). The 3/2 way valve (2) of the left-hand element closes the channel for the carrier fluid (3) and allows washing fluid to flow from the inflow (21) through the central bore (4) and the 2/2 way valve (5) into the main channel (7). The washing fluid flows from there through the 3/2 way valve (23) into the disposal channel (22).

FIG. 3 shows a joint free of lost space and gaps between the individual elements (26a, 26b). The recess (28) has a conically shaped bottom (41) which ensures a maximum sealing effect of the preferably rectangular shaped sealing elements (30) towards the inside to the fluid carrying channel (29) and therefore renders possible the formation of a gap-free transition (42) between the individual elements (26).

FIG. 4 illustrates the example of a sensor (31) which is fitted into a conical bore (32) of the individual element (26) and which projects into the main channel (7) free of lost space and gaps. The sensor (31) is fitted inside a sleeve (33) and is retained together with the latter in the conical bore (32), either self-locking or by means of a clamping element (34).

FIG. 5 illustrates a preferred embodiment of the additional element (35) for the supplementary installation of a sensor as applicable to a pressure sensor (36). The element (35) is connected to an element (26) by means of a flange in place of the connection nipple (43) for the supply lines (37). The fluid flows from or to, respectively, the channel (38) of the element (26) into the channel (39) of the sensor element (35), preferably passing by a pressure sensor (36), the jointing seal of which is free of lost space and gaps on account of the conical shape of the recess (40) and a rectangular seal (30), as illustrated in FIG. 3.

What is claimed is:

1. A modular control assembly for fluid distribution in analytical procedures, said modular control assembly comprising:

a plurality of individual elements, each of the individual elements having a block shape with a valve coupling side, at least one connection side adjoining the valve coupling side and two opposing sides adjoining both the valve coupling and the at least one connection sides, all of the individual elements having identical outer dimensions;

a first channel in each of the individual elements between the valve coupling side and a second channel separated from the valve coupling side by a predetermined distance, the second channel having an opening in the at least one connection side;

a third channel in each of the individual elements connecting the valve coupling side to a side adjoining the valve coupling side and different from the at least one connection side;

each individual element having a valve coupled to the valve coupling side to control fluid communication between the first channel and the third channel;

means for connecting the second channels of the plurality of individual elements to each other; and recesses with a conically shaped bottom formed in the individual elements around the channels for accommodating sealing elements provided for sealing the channels;

wherein the predetermined distance between the valve coupling side and the second channel is the same for all of the individual elements and the second channel of at least one of the individual elements is located closer to one of the two opposing sides such that connecting the second channels of the plurality of individual elements leads to either an in-line arrangement or a staggered arrangement of the individual elements with different function modes of the control assembly being achieved by the in-line and staggered arrangements of the individual elements, the in-line arrangement having the valve coupling sides and the two opposing sides of all of the plurality of individual elements aligned with each other and the staggered arrangement having the valve coupling sides of all of the plurality of individual elements aligned with each other with at least one of the individual elements having its two opposing sides offset relative to the two opposing sides of the other individual elements.

2. The modular control assembly according to claim 1, wherein the sealing elements are rectangular shaped sealing elements.

3. The modular control assembly according to claim 1, further comprising a separate sensor element connected to the third channel of one of the individual elements.

4. The modular control assembly according to claim 1, further comprising a conical bore in one of the plurality of individual elements separated from the second channel by a pierceable layer of material, the layer being pierced before installation of a sensor.

5. The modular control assembly according to claim 4, wherein an assembly comprising a sensor located in a sleeve is retained self locking in the conical bore.

6. The modular control assembly according to claim 4, wherein an assembly comprising a sensor located in a sleeve is retained in the conical bore by means of a clamping element.

7. The modular control assembly of claims 5 or 6, wherein the sleeve is in contact with the conical bore and the contact pressure therebetween is greatest in the area adjacent the second channel.

8. The modular control assembly according to claim 7, wherein the sensor protrudes into the second channel without lost space or gaps.

* * * * *